(12) United States Patent
Wang et al.

(10) Patent No.: US 7,869,013 B2
(45) Date of Patent: Jan. 11, 2011

(54) SURFACE PLASMON RESONANCE AND QUARTZ CRYSTAL MICROBALANCE SENSOR

(75) Inventors: Guangyu Wang, Singapore (SG); Xiaodi Su, Singapore (SG); Wolfgang Knoll, Mainz (SG); Ying-Ju Wu, Singapore (SG)

(73) Assignees: Agency for Science, Technology and Research, Singapore (SG); Max-Planck-Gesellschaft zur Forderung der Wissenschaften E. V. (DE)

( * ) Notice: Subject to any disclaimer, the term of this patent is extended or adjusted under 35 U.S.C. 154(b) by 607 days.

(21) Appl. No.: 11/662,826

(22) PCT Filed: Sep. 15, 2004

(86) PCT No.: PCT/SG2004/000296

§ 371 (c)(1),
(2), (4) Date: Jan. 17, 2008

(87) PCT Pub. No.: WO2006/031198

PCT Pub. Date: Mar. 23, 2006

(65) Prior Publication Data

US 2008/0163688 A1    Jul. 10, 2008

(51) Int. Cl.
*G01N 21/00* (2006.01)

(52) U.S. Cl. .................................................. 356/73
(58) Field of Classification Search ............. 356/445; 257/416, 414, E27.006; 73/580
See application file for complete search history.

(56) References Cited

U.S. PATENT DOCUMENTS

| | | | |
|---|---|---|---|
| 5,351,127 A | 9/1994 | King et al. |
| 5,869,748 A | 2/1999 | Stevenson et al. |
| 6,161,437 A | 12/2000 | Brennan et al. |
| 6,294,391 B1 | 9/2001 | Badley et al. |
| 6,495,328 B2 | 12/2002 | Nakamura et al. |

(Continued)

FOREIGN PATENT DOCUMENTS

DE    10024366    1/2002

(Continued)

OTHER PUBLICATIONS

Anonymous, "Soft' Materials and Patterning Techniques for Photonics" Presentation, University of Illinois at Urbana/Champaign.

(Continued)

*Primary Examiner*—Tarifur Chowdhury
*Assistant Examiner*—Abdullahi Nur
(74) *Attorney, Agent, or Firm*—Quarles & Brady LLP

(57) ABSTRACT

A sensor chip assembly for use in a sensor capable of Surface Plasmon Resonance (SPR) and gravimetric sensing. The assembly comprising a transparent piezoelectric substrate (1) having a first surface and a second surface opposite to the first surface. The assembly also comprising first and second thin film metal electrodes (2,3) respectively provided on the first and second surfaces of the substrate (1). The second thin film metal electrode (3) being position on the second surface of the substrate (1) such that a light beam is capable of being transmitted through the second surface of the substrate and reflected from the first thin film metal electrode. The assembly also comprising an attenuated total reflection (ATR) coupler (11) disposed adjacent to the second thin film metal electrode (3).

16 Claims, 11 Drawing Sheets

U.S. PATENT DOCUMENTS

2004/0113077 A1* 6/2004 Franzen et al. ........... 250/338.1

FOREIGN PATENT DOCUMENTS

| DE | 20113591 | 3/2002 |
|---|---|---|
| EP | 1058109 | 6/2000 |
| WO | 0237109 | 5/2002 |
| WO | 03091713 | 11/2003 |

OTHER PUBLICATIONS

Bolle, G. et al., "A Photometer form the Measurement of Elastically Scattered Light from Macromolecules in Solution," IEEE Transactions on Instrumentation and Measurement, 1994, 43:553-557.

Lashitsch, A. et al., "Simultaneous determination of optical and acoustic thickness of protein layers using surface plasmon resonance spectroscopy and quartz crystal microweighing," Applied Physics Letters, 2000, 77:2252-2254.

Resnick, A., "Use of optical tweezers for colloid science," J of Colloid and Interface Science, 2003, 262:55-59.

Weber, M.J., CRC handbook of Laser Science Technology—Supplement 2—Optical Materials, p. 100.

The State Intellectual Property Office of the People's Republic of China, First Office Action for Patent Application 200480044409.8, Mar. 6, 2009.

The State Intellectual Property Office of the People's Republic of China, Second Office Action for Patent Application 200480044409.8, Sep. 4, 2009.

The State Intellectual Property Office of the People's Republic of China, Third Office Action for Patent Application 200480044409.8, Dec. 25, 2009.

* cited by examiner (a)

(b)

SURFACE PLASMON RESONANCE AND QUARTZ CRYSTAL MICROBALANCE SENSOR

TECHNICAL FIELD

The present invention generally relates to a sensor for sensing a biological, biochemical or chemical sample. More particularly, the present invention relates to a sensor that is capable of sensing a biological, biochemical or chemical sample using Surface Plasmon Resonance and microgravimetric sensing techniques.

BACKGROUND

Surface Plasmon Resonance (SPR) and Microgravimetric sensing techniques, such as Quartz Crystal Microbalance, are known independently as methods suitable for in-situ, label free sensing and analysis of binding reactions. Sensors using SPR or QCM have been used to analyse biological, biochemical and chemical samples.

QCM devices comprise a quartz crystal wafer having two planar metal electrodes disposed on the two surfaces of the wafer. The sample to be analysed is adsorbed onto the surface of one of the electrodes. The shift in the quartz crystal can be excited to mechanical resonance by an alternating an electric field due to the inverse piezoelectric effect. The resonance frequency is dependent upon the mass of material adsorbed onto the surface electrode. For instance, the resonance frequency decreases for mass accumulation and increases for mass reduction. The shift in frequency can be related to the adsorbed mass using analytical equations. A mass loading in the order of about 1 ng/cm2 can be detected.

SPR is a known method for the detection of chemical changes occurring at the surface of a thin metal film. SPR measures changes in the optical thickness (i.e. refractive index) arising from molecular adsorption on the metal surface. In SPR, an evanescent wave (which is an exponential-decaying wave) exists at the sensor surface. In what is known as the Kretchmann geometry, an evanescent wave is generated when total internal reflection of incident light occurs at the interface of a substance with a high refractive index and a substance of low refractive index (i.e. a glass-air interface of a prism). SPR occurs under certain conditions when a thin film of metal (e.g. gold or silver) is placed on the surface. When the incident light is monochromatic, the free electrons of the metal will oscillate (ie. a surface plasmon is excited) and absorb energy corresponding to a certain angle of incident light. The angle is called the SPR angle. The SPR signal is detected by measuring the intensity of the reflected light. At the SPR angle, a sharp decrease or "dip" in intensity is measured as the surface plasmon absorbs energy.

The position of the SPR angle depends on the refractive index of the sensing surface which changes upon the binding of molecules to the surface. Consequently, the SPR angle changes according to the amount of molecules bound to the surface. The detection limitation of SPR is approximately 1 ng/cm2.

SPR and QCM techniques each have their own specific strengths, weaknesses and have assumptions that are inherent in data collection and analysis. Accordingly, each technique is sensitive to different properties of a thin film sample.

Analytical devices that utilise both SPR and QCM techniques are known. German patent DE 10024366 discloses an analytical devices that combines SPR and QCM using a grating coupler. The use of a grating coupler requires that the incident light beam pass through the sample solutions for SPR, requiring the flow-cell and the sample be optically transparent. This has the disadvantage of the results having a low signal/noise ratio. Moreover the SPR measurement sensitivity is low compared to prism-coupler SPR sensors.

There is a need to provide a sensor and an analytical technique, which overcomes, or at least ameliorates, one or more of the disadvantages described above.

SUMMARY OF INVENTION

According to a first aspect of the invention, there is provided a sensor chip assembly for use in a sensor capable of Surface Plasmon Resonance (SPR) and gravimetric sensing of a sample, the assembly comprising:

a transparent piezoelectric substrate having a first surface and a second surface opposite to the first surface;

a first thin film metal electrode provided on the first surface of the substrate for contact with said sample; and a second thin film metal electrode provided on the second surface of the substrate, said second thin film metal electrode being disposed on said substrate such that a light beam is capable of being transmitted through the second surface of the substrate and reflected from the first thin film metal electrode; and an attenuated total reflection (ATR) coupler disposed adjacent to the second thin film metal electrode for coupling light to said substrate; and a light coupling medium disposed between the ATR coupler and the substrate, said light coupling medium substantially matching the refractive index of the ATR coupler and the substrate and having a low viscosity relative to an index matching oil having a viscosity of 100 cP, wherein in use, a gravimetric signal is generated by applying an oscillating electric field to said first and second thin film metal electrodes and an SPR signal is generated by reflecting a light beam from said first thin film metal electrode that has been transmitted through said ATR coupler, said light coupling medium and said substrate.

In one embodiment, there is provided an assembly for use in a sensor capable of Surface Plasmon Resonance (SPR) and gravimetric sensing, the assembly comprising:

a transparent piezoelectric substrate having a first surface and a second surface opposite to the first surface;

a first thin film metal electrode provided on the first surface of the substrate;

a second thin film metal electrode provided on the second surface of the substrate;

an attenuated total reflection (ATR) coupler disposed adjacent to the second thin film metal electrode; and a light coupling medium disposed between the ATR coupler and the second thin film metal electrode to substantially match the refractive index of the ATR coupler and the substrate.

According to a second aspect of the invention, there is provided a sensor comprising:

a transparent piezoelectric substrate having a first surface and a second surface opposite to the first surface;

a first thin film metal electrode provided on the first surface of the substrate for locating a sample thereon, and a second thin film metal electrode provided on the second surface of the substrate, the first and second thin film metal electrodes capable of being coupled to an oscillator circuit for oscillating an electric field at one or more selected frequencies to thereby cause the substrate to resonate; and an attenuated total reflection (ATR) coupler disposed adjacent to the second thin film metal electrode and capable of optically coupling a light beam, at a plurality of incident angles, from a light beam source, to the first thin film metal electrode to generate surface plasmon resonance (SPR) upon excitation; and a light coupling medium disposed between the ATR coupler and the substrate, said light coupling medium substantially matching the refractive index of the ATR coupler and the substrate and having a low viscosity relative to an index matching oil having a viscosity of 100 cP wherein in use, a gravimetric signal is generated by applying the oscillating electric field to said first and second thin film metal electrodes and an SPR signal is generated by reflecting a light beam from said first thin film metal electrode that has been transmitted through said ATR coupler, said light coupling medium and said substrate.

In one embodiment, the sensor may further comprise a light coupling medium disposed between the ATR coupler and the second thin film metal electrode to substantially match the refractive index of the ATR coupler and the substrate.

According to a third aspect of the invention, there is provided a Surface Plasmon Resonance (SPR) and gravimetric analysis sensing method using a sensor comprising: a transparent piezoelectric substrate having a first surface and a second surface opposite to the first surface; a first thin film metal electrode provided on the first surface of the substrate, and a second thin film metal electrode provided on the second surface of the substrate; and an attenuated total reflection (ATR) coupler adjacent to the second thin film metal electrode, and a light coupling medium disposed between the ATR coupler and the substrate, said light coupling medium substantially matching the refractive index of the ATR coupler and the substrate and having a low viscosity relative to an index matching oil having a viscosity of 100 cP, the method comprising the steps of:

providing a sample on the first thin film metal electrode;

oscillating an electric field through the first and second thin film metal electrodes at one or more selected frequencies to generate a gravimetric signal to thereby cause the substrate to resonate; and generating an SPR signal from a reflecting a light beam, at a plurality of incident angles, reflected from the first thin film metal electrode after being transmitted through said ATR coupler, said light coupling medium and said substrate to generate surface plasmon resonance (SPR).

In one embodiment, the method may further comprise the step of providing a light coupling medium between the ATR coupler and the second thin film metal electrode to substantially match the refractive index of the ATR coupler and the substrate.

According to a fourth aspect of the invention, there is provided a method of fabricating an assembly for use in a sensor capable of Surface Plasmon Resonance (SPR) and gravimetric sensing, the method comprising:

depositing a first thin film metal electrode on a first surfaces of a transparent piezoelectric substrate;

depositing a second thin film metal electrode on a second surfaces, opposite to the first surface, of the substrate such that a light beam is capable of being transmitted through the second surface of the substrate and reflected from the first thin film metal electrode; and attaching an attenuated total reflection (ATR) coupler adjacent to the second thin film metal electrode; and sealing a light coupling medium disposed between the ATR coupler and the substrate, said light coupling medium substantially matching the refractive index of the ATR coupler and the substrate and having a lower viscosity relative to an index matching oil having a viscosity of 100 cP.

In one embodiment, the method may further comprise the step of sealing a light coupling medium between the ATR coupler and the second thin film metal electrode to substantially match the refractive index of the ATR coupler and the substrate.

According to a fifth aspect of the invention, there is provided a sensor system capable of performing surface plasmon resonance (SPR) and gravimetric sensing on a biological, biochemical or chemical sample, the sensing system comprising:

a housing having a chamber for locating the sample therein;

a transparent piezoelectric substrate having a first surface and a second surface opposite to the first surface;

a first thin film metal electrode provided on the first surface of the quartz substrate and in fluid communication with the chamber;

a second thin film metal electrode provided on the second surface of the quartz substrate, said second thin film metal electrode being disposed on said substrate such that a light beam is capable of being transmitted through the second surface of the substrate and reflected from the first thin film metal electrode;

an oscillator circuit, coupled to the first and second thin film metal electrodes, for oscillating an electric field at one or more selected frequencies to cause the substrate to resonate at a resonate frequency;

a resonate frequency detector for detecting the resonate frequency to enable a gravimetric signal to be detected;

a light beam source for generating a light beam at a plurality of incident angles;

an attenuated total reflection (ATR) coupler disposed adjacent to the second thin film metal electrode for optical coupling to the light beam source such that an internally reflected light beam is reflected from the first thin film metal electrode at an angle of incidence which will cause surface plasmon resonance (SPR) to occur a light coupling medium disposed between the ATR coupler and the substrate, said light coupling medium substantially matching the refractive index of the ATR coupler and the substrate and having a lower viscosity relative to an index matching oil having a viscosity of 100 cP; and a detector for receiving the internally reflected light beam and for detecting the characteristics of SPR that are dependent on the reaction between the sample and the first thin film metal electrode.

In one embodiment, sensor system comprises light coupling medium between the ATR coupler and the second thin film metal electrode to substantially match the refractive index of the ATR coupler and the substrate.

According to a sixth aspect of the invention, there is provided a method for Surface Plasmon Resonance (SPR) and gravimetric sensing of a sample liquid using a sensor, the sensor comprising: a transparent piezoelectric substrate having a first surface and a second surface opposite to the first surface; a first thin film metal electrode provided on the first surface of the substrate; a second thin film metal electrode provided on the second surface of the substrate; and an attenuated total reflection (ATR) coupler disposed adjacent to the second thin film metal electrode and a light coupling medium disposed between the ATR coupler and the substrate, said light coupling medium substantially matching the refractive index of the ATR coupler and the substrate and having a lower viscosity relative to an index matching oil having a viscosity of 100 cP; the method comprising the steps of:

(a) providing the sample liquid on the first thin film metal electrode;
(b) transmitting a light beam through the ATR coupler, the light coupling medium and the substrate;
(c) for reflecting the transmitted light from the first thin film metal electrode;
(d) detecting the intensity of reflected light to generate an SPR signal;
(e) applying an electric field across the first and second thin film metal electrodes; and
(f) measuring the resonant frequency of the electric field to generate a gravimetric signal.

DISCLOSURE OF EMBODIMENTS

The transparent piezoelectric substrate may comprise a material selected from the group consisting of: quartz, lithium tantalate and lithium niobate.

Any metal that is capable of resonating with light at a particular wavelength to produce SPR may be used as the thin film metal electrode. The thin film metal electrode material may be selected from the group consisting of: aluminum; chromium; cobalt; copper; gold, indium, molybdenum; nickel; palladium; platinum; silver; tin; titanium; tungsten and zinc.

The light coupling medium may be any transparent liquid that has a refractive index in the range selected from the group consisting of: 1.50 to 1.60, 1.51 to 1.59, 1.52 to 1.58, 1.52 to 1.57, 1.52 to 1.56, 1.52 to 1.55, 1.53 to 1.55. In an embodiment where the substrate is quartz, the light coupling medium may have a refractive index of about 1.54 at wavelength of 632.8 nm.

A cavity may exist between the substrate and the ATR coupler, which may be filled with the index matching medium and sealed. The distance between the substrate and the ATR coupler may be in the range selected from the group consisting of: 0.5 mm to 2.5 mm; 0.75 mm to 2.25 mm; and 1 mm to 2 mm. The light coupling medium may have a low density relative to that of water, the density may be within the range selected from the group consisting of: 1.05 to 1.3; 1.1 to 1.25; and 1.1 to 1.2.

The light coupling medium may be an aqueous medium or a non-aqueous medium. In one embodiment, the light coupling medium is a hydrocarbon having carbon atoms in the range selected from the group consisting of: 1 to 25; 2 to 20; 3 to 18; 4 to 15; 5 to 12; and 5 to 10. The light coupling medium may be selected from the group consisting of: styrene, toluene, benzyl alcohol, and butylbenzene, tetrahydronaphthalene, acetophenone, benzonitrile, dibromomethane, benzylamine, 3-pyridinemethanol, 2-methylbenzenemethanamine, phenyloxirane.

The light coupling medium may have a relative density to water in the range selected from the group consisting of: 1.05 to 1.3; 1.1 to 1.25; and 1.1 to 1.2.

In one embodiment, the second thin film metal electrode may be provided with at least one opening for allowing the light beam to be transmitted therethrough. The second thin film metal electrode may be provided with a plurality of openings. The opening may be large enough to allow multiple light beams to pass therethough and to be reflected by the interface between the substrate and the first thin film metal electrode.

The gravimetric sensing may be selected from the group consisting of: quartz crystal microbalance sensing; surface acoustic wave sensing; bulk acoustic wave sensing.

In one embodiment, there is provided a ATR coupler may be a prism having a shape selected from the group consisting of: substantially hemispherical, substantially rectangular, substantially square, and substantially cylindrical.

BEST MODE

Non-limiting examples of the invention, including the best mode, and a comparative example will be further described with reference to the accompanying drawings in which:—

Figure 7:
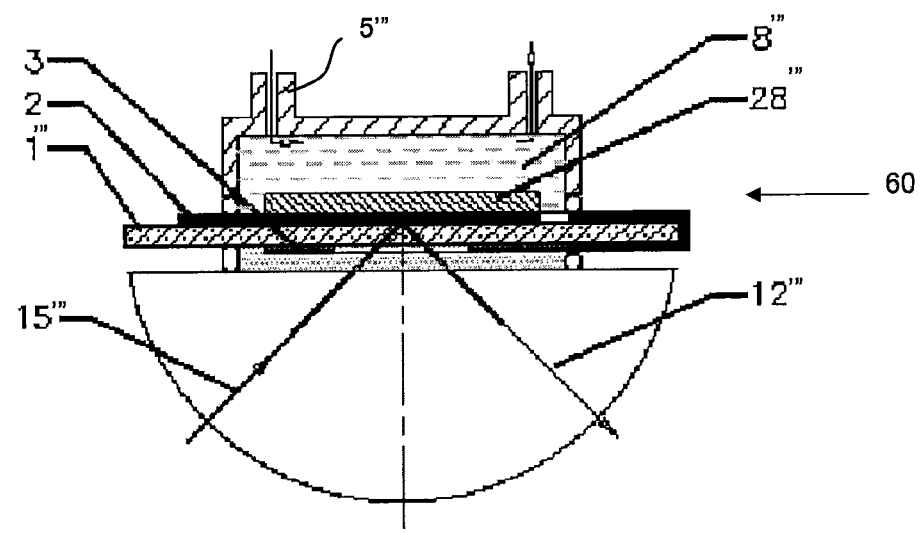
Figure 8:
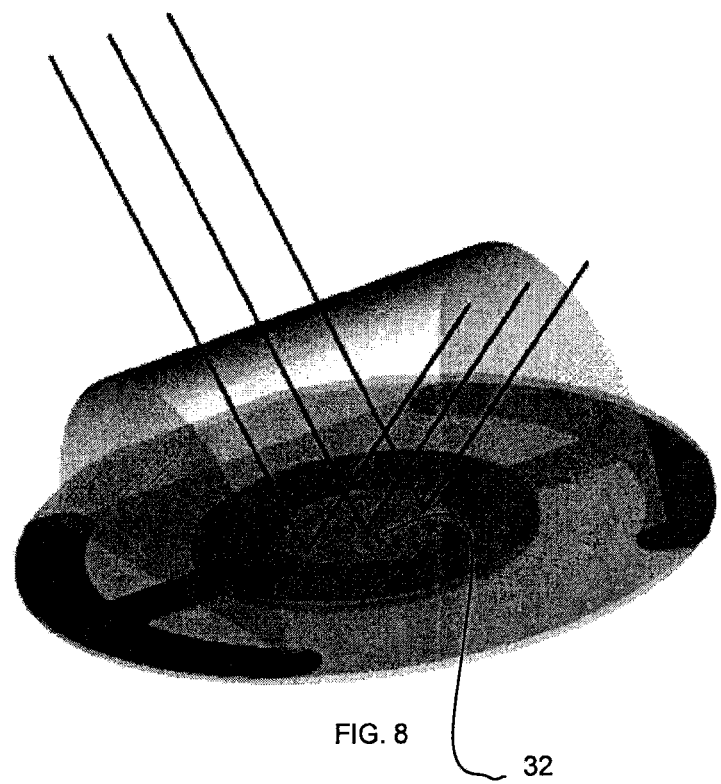
Figure 9:
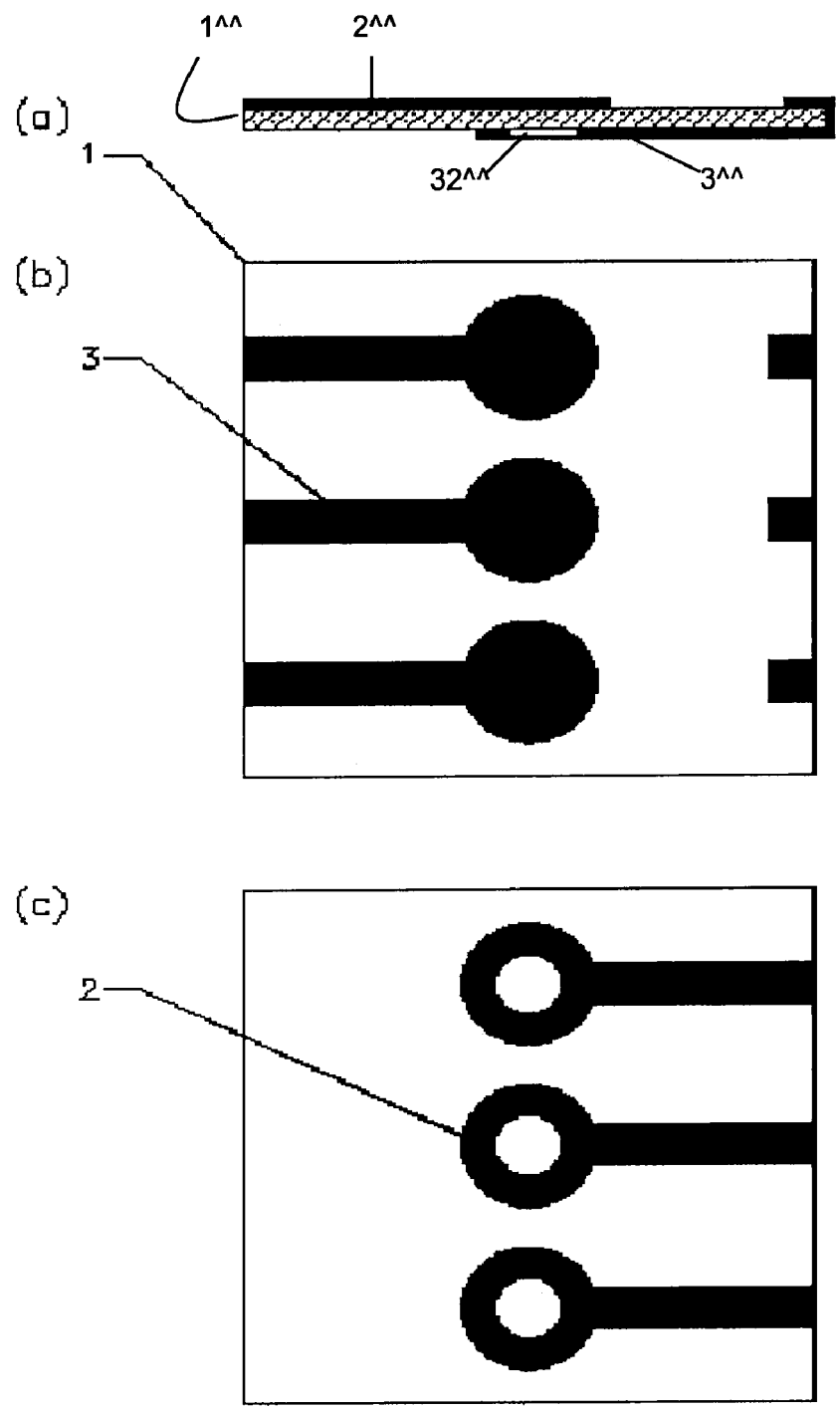
Figure 10A:
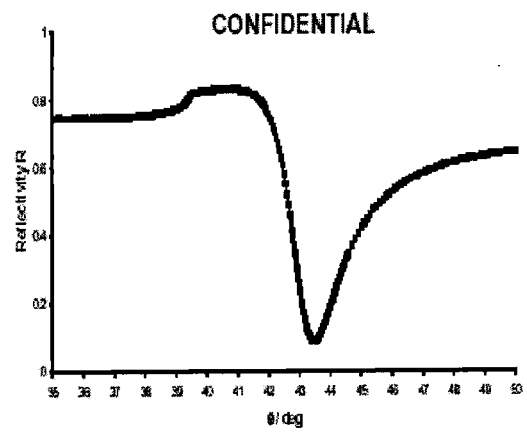
Figure 10B:
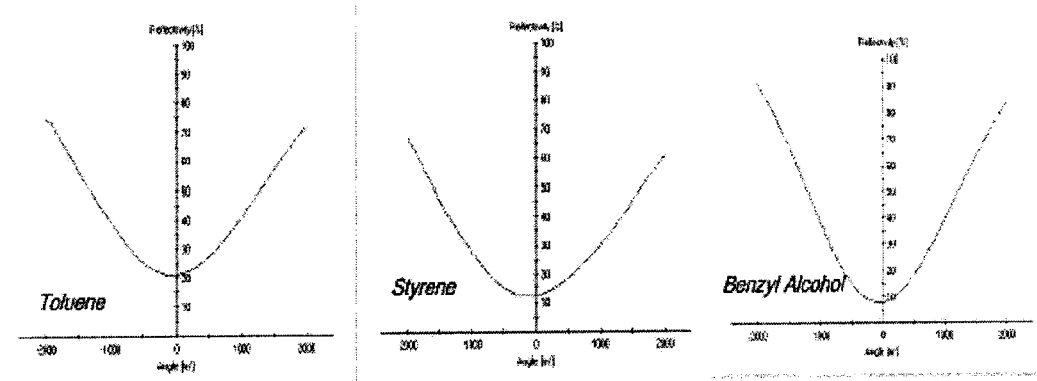

FIG. 4A-D are respectively, cross-sectional views of four different ATR optical coupling SPR configurations;

FIG. 5A is a cross-sectional view of another embodiment of a sensor chip capable of combined simultaneous QCM and SPR;

FIG. 5B is a plan view of the sensor chip of FIG. 5A;

FIG. 5C is a cross-sectional view of another embodiment of a Kretschmann configuration ATR optical coupling arrangement using the sensor chip of arrangement of FIG. 5A;

FIG. 6A is a cross-sectional view of another embodiment of a Kretschmann configuration ATR optical coupling arrangement that is disposable, using the sensor chip arrangement of FIG. 5A;

FIG. 6B is the plan view of the sensor chip and Kretschmann configuration ATR optical coupling arrangement of FIG. 6A;

FIG. 7 is a cross-sectional view of another embodiment of a sensor apparatus for performing QCM and SPR analytical techniques, which utilizes the sensor chip of FIG. 1;

FIG. 8 is a cross-sectional view of another embodiment of a sensor apparatus for performing multi-mode measurement of QCM and SPR analysis;

FIG. 9A is a cross-sectional view of another embodiment that discloses an array of metal electrodes provided on a quartz substrate;

FIG. 9B is a plan view of an array of metal electrodes provided on a top surface of the quartz substrate;

FIG. 9C is a bottom view of an array of metal electrodes having openings provided therein, the metal electrodes being provided on a bottom surface of the quartz substrate;

FIG. 10A shows an angular scan curve obtained from the sensor chip of FIG. 1 using toluene for index matching;

FIG. 10b shows three angular scan curves obtained from the sensor chip of FIG. 1 respectively for toluene, styrene and benzyl alcohol for index matching.

Figure 3:
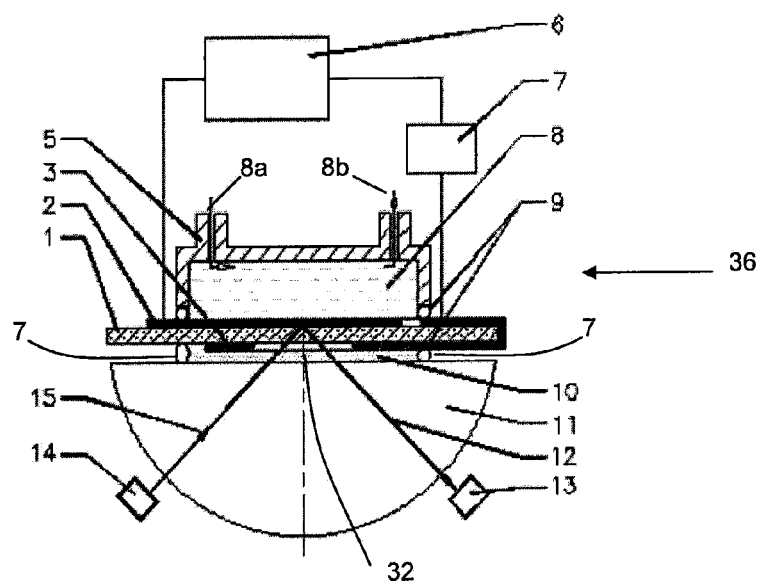
FIG. 3 is a cross-sectional view of a sensor apparatus for performing QCM and SPR analytical techniques, which utilizes the sensor chip of FIG. 1.
Figure 4:
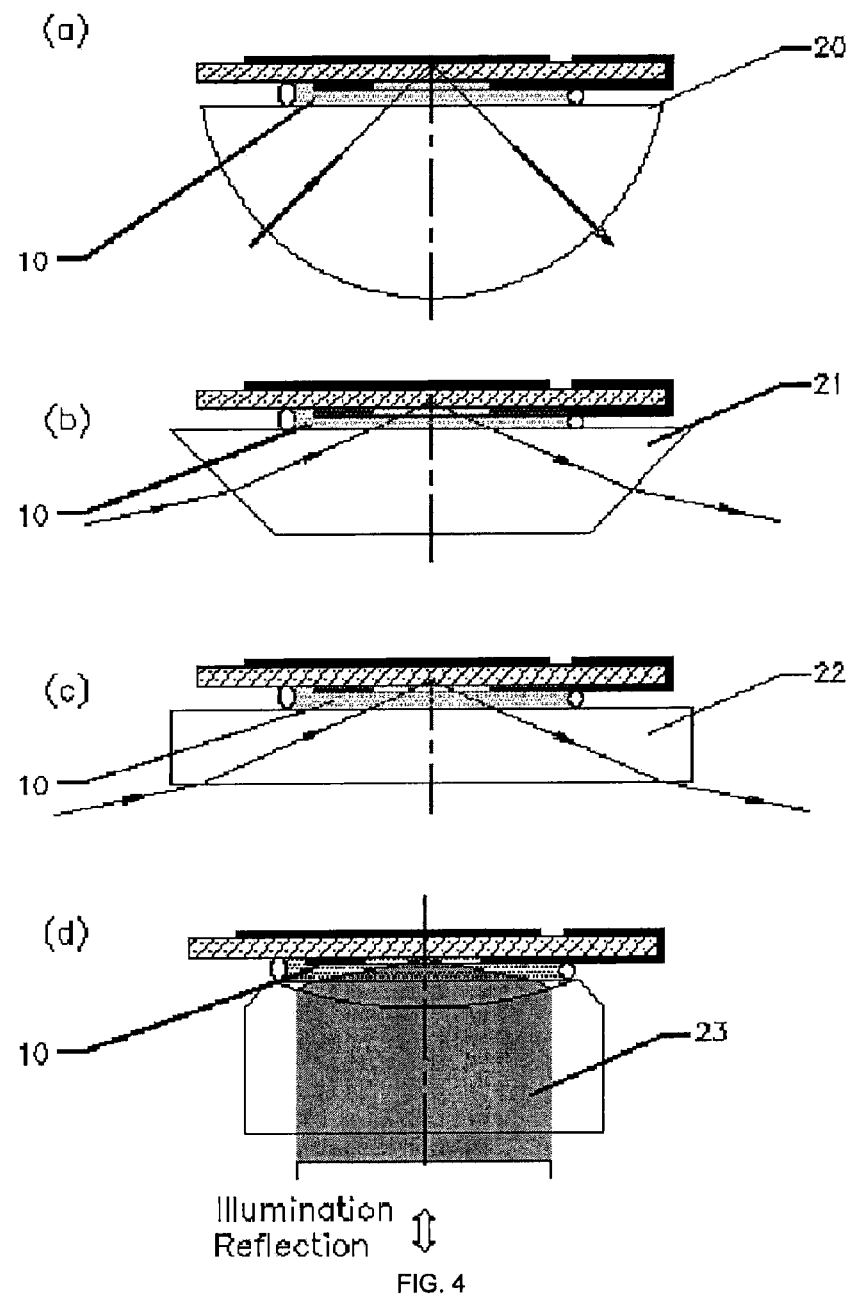
Figure 10C:
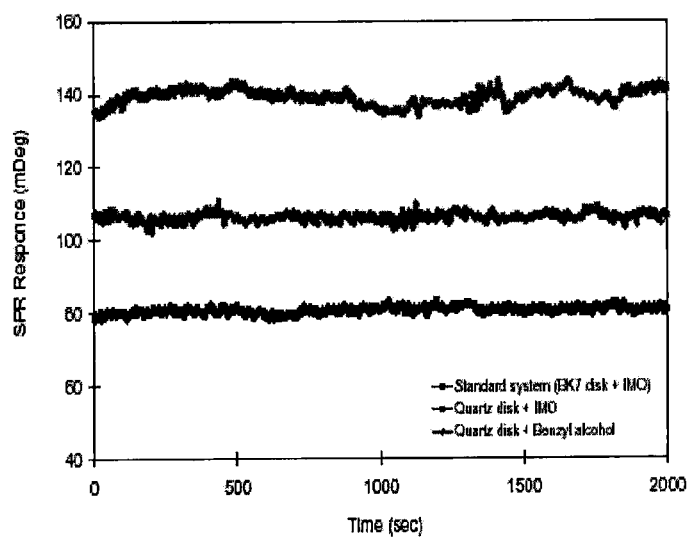
Figure 12:
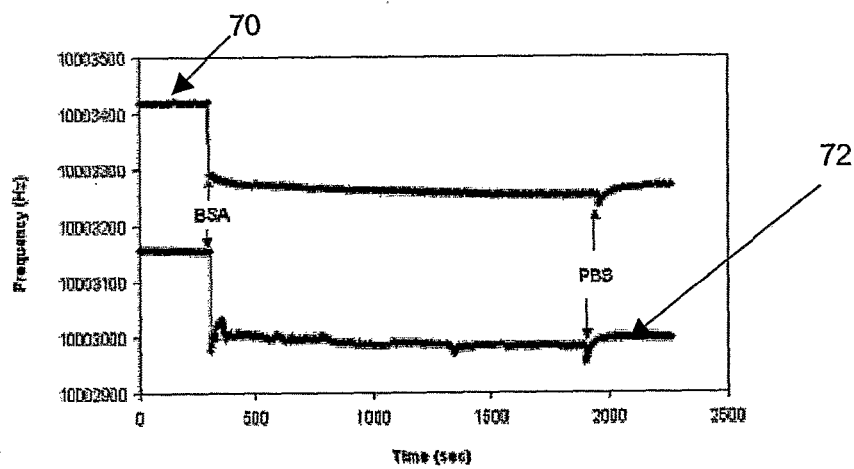
Figure 13:
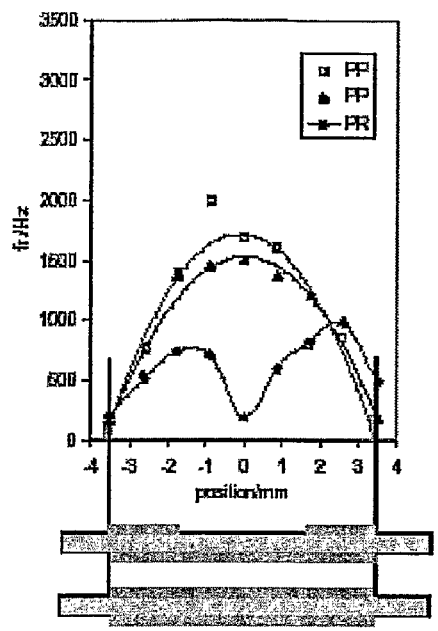
Figure 14:
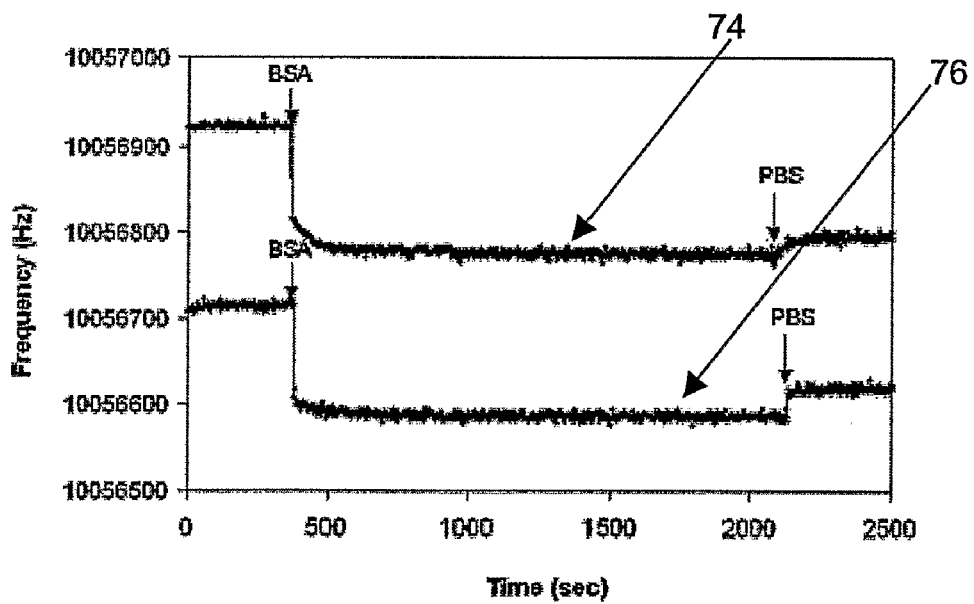
Figure 15:
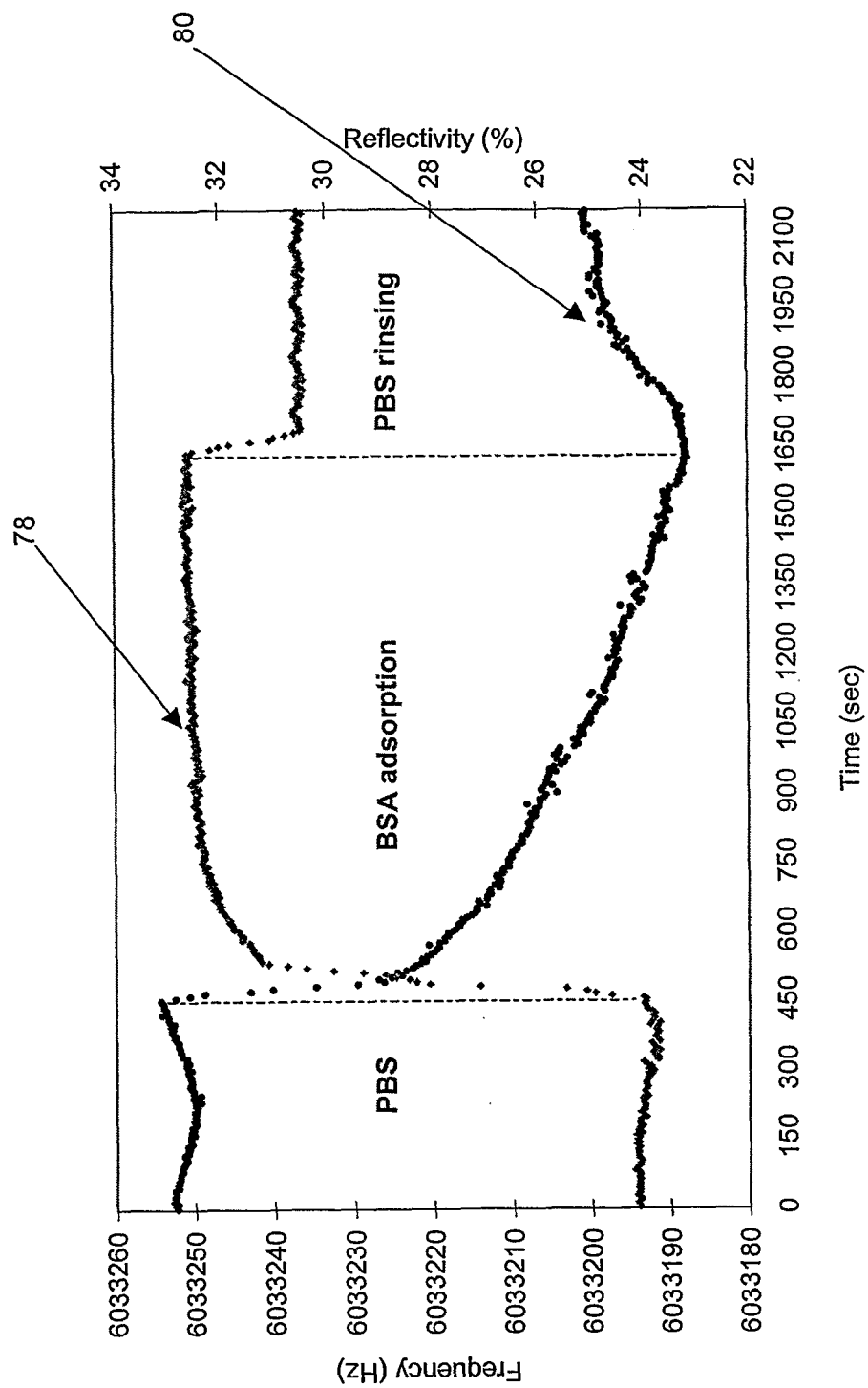

FIG. 10c shows SPR stability measured from an Autolab SPR instrument;

FIG. 11A shows a graph of simultaneous frequency and motional resistance responses of QCMs with the exposures in which the quartz crystal has a lower face exposed to air;

FIG. 11B is a graph showing simultaneous frequency and motional resistance responses of QCMs with the exposures of in which the quartz crystal has a lower face exposed to toluene;

FIG. 12 is a graph showing a frequency response of activated QCMs to BSA adsorption from a PBS buffer on an upper electrode;

FIG. 13 is a graph showing the radial dependent mass sensitivity on QCMs;

FIG. 14 is a graph showing the frequency response of the P/P and P/R electroded QCMs to BSA adsorption reaction;

FIG. 15 is a graph showing the frequency response of simultaneous SPR and QCM signals of the sensor apparatus of FIG. 3.

DETAILED DESCRIPTION OF DISCLOSED EMBODIMENTS

Figure 1A:
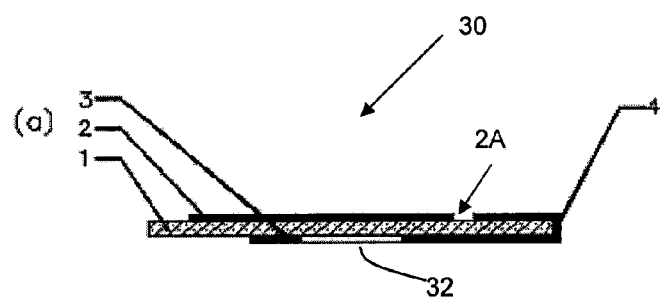
FIG. 1A is a cross-sectional view of a sensor chip capable of combined simultaneous QCM and SPR.
Figure 1B:
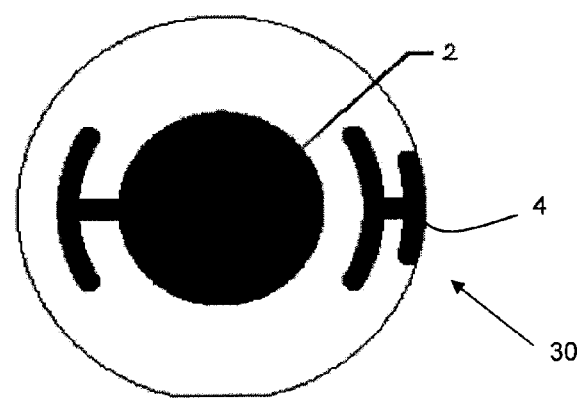
FIG. 1B is a plan view of the sensor chip of FIG. 1A.

FIGS. 1A, 1B and 1B disclose a sensor chip arrangement shown generally by arrow 30 that is capable of being used in an sensor system that is capable of utilising combined SPR and Quartz Crystal Microbalance (QCM) gravimetric sensing.

The sensor chip 30 comprises a transparent piezoelectric substrate in the form of a quartz substrate 1. A first thin film metal electrode in the form of electrode 2 is provided on the top side of the substrate 1. A second thin film metal electrode in the form of electrode 3 is provided on the opposite side of the substrate 1. The electrode 3 is provided with an opening 32 to allow transmission of laser light onto the substrate 1 as will be described further below.

Figure 1C:
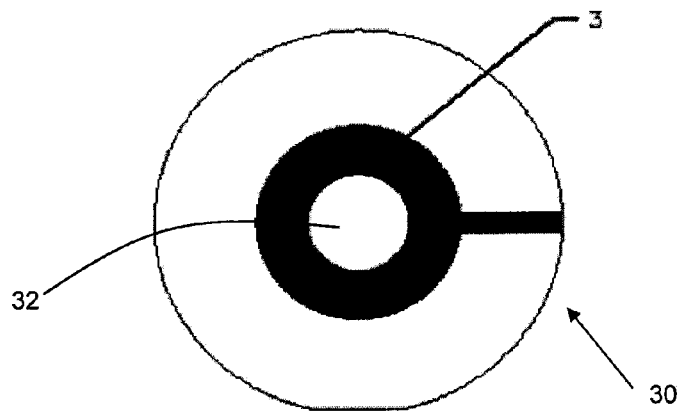
FIG. 1C is a bottom view of the sensor chip of FIG. 1A.

The electrode 3 is connected to a metal strip 4 that wraps around the right edge of the quartz substrate 1 as shown in FIG. 1. A gap 2A is provided on the substrate 1 to allow a sample to contact the substrate 1 in use. The metal strip 4 enables electrode 3 to be electrically connected from one side. The electrodes (2,3) and quartz substrate 1 enable QCM sensing to be performed. As show in the FIG. 1C, the opening 32 (or "window") at the center of electrode 3 enables SPR analysis to be conducted by allowing a beam of incident light to pass through the quartz substrate 1 so that, at a particular incident angle, the light beam undergoes total internal reflection to excite surface plasmon resonance (SPR) at the surface of the sensing electrode 2. It will be appreciated that the opening 32 allows light to pass directly onto the substrate 1.

Figure 2:
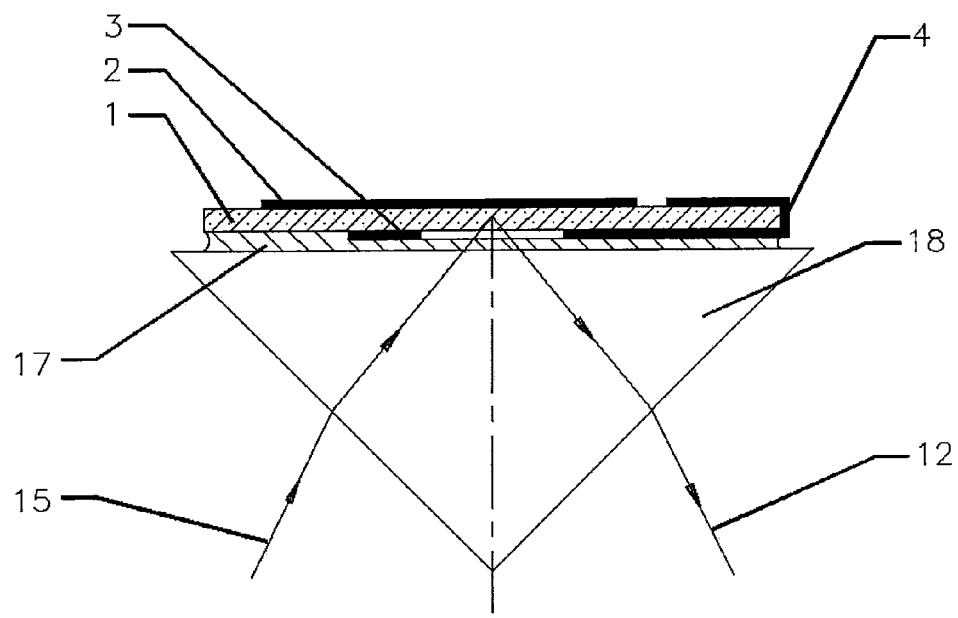
FIG. 2 is a schematic drawings of a Kretschmann configuration ATR optical coupling arrangement for SPR.

FIG. 2 shows an Attenuated Total Reflection (ATR) prism coupler for SPR analysis. The arrangement of FIG. 2 is referred to as "Kretschmann arrangement" and includes a prism 18, on the base surface of which is mounted a sensing disk 16, which is made from material having same refractive index of the prism 18. The air gap between the sensing disk and prism 18 is filled with a quantity of index matching fluid 17 for light coupling. The index matching fluid 17 between the quartz substrate 1 and the prism 18 is used to enhance the quality of the SPR signal that is generated upon SPR excitation, in particular by reducing any noise associated with the generated SPR signal due to refraction affects. In particular, an increase in the distance between the quartz substrate 1 and the prism 18 from 5 nm to 15 nm to create an air gap, can significantly increase the oscillation of the SPR signal, and therefore the quality of the signal.

The upper surface of the sensing disk is coated with a thin metal layer 19 (e.g gold). This layer 19 provides the conductive surface layer in which, in use, surface plasmons are excited.

FIG. 3 is a cross-sectional view of a sensor system 36 for performing SPR and QCM sensing. In this embodiment, the SPR and QCM sensing is performed simultaneously. The sensor chip 30 of FIG. 1 is shown as being clamped between an attenuated total reflection (ATR) coupler in the form of prism 11 in a Kretschmann configuration and a sample receiving cell in the form of cell 5 that comprises a chamber for receiving a sample 8. The cell 5 is exposed to the electrode 2. The cell also includes a sample inlet conduit 8a and a sample outlet conduit 8b for respectively receiving and permitting outflow of the sample. In this disclosed embodiment, the sample is an liquid analyte sample 8. However, in other embodiments, the sample may be in the form of a gas.

The sensor chip 30 is clamped to the prism 11 and the cell 5 by two O-rings (7,9).

A cavity is provided between the prism 11 and electrode 3, which is filled with a light coupling medium in the form of index matching liquid 10.

Light is directed to the prism assembly from a light source in the form of laser 14. In this embodiment, the laser 14 has an output wavelength in the range 500 nm to 900 nm. The incident beam 15, passes through the index matching liquid 10 and quartz substrate 1 and refracts at the interface of the quartz substrate 1 and the electrode 3. A reflection beam 12 passes back through the prism 11 to a detector 13.

Under certain conditions, the light undergoes total internal reflection at the interface of the quartz substrate 1 and the electrode 3, causing SPR. Accordingly, adsorption of the analyte solution 8 can be monitored while it is exposed to the sensing electrode 3.

The sensor system 36 also includes an oscillation circuit 6 and a frequency counter 7, which are utilised for performing QCM analysis. An electric field in the form of an AC power supply (not shown) is applied from the circuit 6 to the electrodes (2,3) over the quartz substrate 1 to stimulate a shear mode oscillation. This causes adsorption of the analyte solution 8 so that a QCM signal can be obtained. It should be realised that an SPR signal and a QCM signal can be obtained simultaneously or asynchronously.

FIGS. 4A-D illustrate four different ATR coupling based SPR configurations optically coupled to the sensor chip 30. In FIG. 4 (a), there is shown a combination of SPR and QCM using an ATR coupling based SPR technique. This configuration employs a fan-shaped (e.g. hemicylindrical lens) transparent block 20 prism to focus a light beam to illuminate the electrode 3 via an index matching liquid 10. A full disclosure of a fan shaped prim for use in ATR is disclosed in EP-A1-0305109, which is incorporated in its entirety by way of reference.

FIG. 4B discloses a configuration that employs a trapezoidal transparent block 21 to focus a light beam to illuminate the electrode 3 via an index matching liquid 10. FIG. 4C discloses a configuration that employs a rectangular transparent block 22 to focus a light beam to illuminate the electrode 3 via an index matching liquid 10. FIG. 4D discloses a configuration employs a cylindrical shaped transparent block 23 to focus a light beam to illuminate the electrode 3 via an index matching liquid 10.

FIG. 5A is a cross-sectional view of a disk arrangement 40 that is compact and which includes the sensor chip 30' coupled to a supporting slide 24 that is provided with a shallow cavity 15. In this embodiment, the sensor chip 30' is functionally similar to the sensor chip 30 and thus like elements are labeled with like reference numerals followed by the prime (') symbol. However, it will be recognized that some differences in structure exist between the sensor chip 30 and the sensor chip 30'. For example, this embodiment shows a shallow cavity 15a' having an oblique angle. The provision of the oblique angle 15b' ensures that the cavity surface is not parallel to the sensor disk to thereby improve QCM performance by minimizing the responses caused by compressional wave resonance.

In this embodiment, a slide 24' is disposed between the substrate 1 and the prism 11'. The slide 241 is made of glass with a refractive index of 1.54 at wavelength of 632.8 nm. The shallow cavity 15' is filled with low viscosity and low density index matching liquid 10'. The sensor chip 30' is cleaved onto the slide 24' to ensure a good sealing.

FIG. 5C shows the disk arrangement 40' attached to prism 11' which is hemispherical in shape, as described for the embodiment of FIG. 4A above. The sensor chip 36' is compact and advantageously can be incorporated into an existing commercialized SPR machine such as an Autolab™ ESPR (electrochemical surface plasmon resonance) analyser manufactured by Eco Chemie B.V. of Utrecht, The Netherlands.

In this embodiment, the supporting slide 24' has a thickness of 0.82 mm, a diameter of 25.4 mm and is made from BK7 glass. The cavity 15 of the slide 24 is disposed at an oblique angle 25 to the surface of the electrode 3'. This is to minimize the responses caused by compressional wave resonance, which can be significant when the liquid depth is as low as ~1 mm (as for the compact sensor disk arrangement of FIG. 5).

The cavity 15a' is filled with an index matching liquid in the form of a styrene solution and covered by the sensor chip 30'. In this embodiment, the sensor chip 30' is a 6 MHz combined SPR and QCM sensor disk having a thickness of 0.276 mm and a diameter of 20 mm. The electrodes (2',3') have a diameter of 10 mm while the electrode (3') has an opening 32' with an internal diameter of 5 mm.

The edge of the disk 30' is sealed with a sealant such as glue. A suitable adhesive would be 3M™ Auto Glass Adhesive from Minnesota Mining & Manufacturing Company, of Maplewood, Minn., United States of America.

The disk arrangement 40' is compact and able to be utilised in an existing SPR instrument such as an Autolab™ SPR machine.

The disk arrangement 40' may be mounted onto the prism 11' by coating a thin layer of index matching oil 17'. The disk arrangement 40' can be used as a biosensor in that it can be used for measuring, biological, biochemical or chemical samples.

In use, SPR and QCM can be measured simultaneously by connecting both the electrodes (2',3') to an oscillator (such as the oscillator 6 shown in FIG. 3) and frequency counter (such as the frequency counter 7 shown in FIG. 3) to initiate QCM as is known in the art. Exemplary QCM methods are disclosed in U.S. Pat. Nos. 6,156,578 and 5,201,215 which are incorporated herein in their entirety for reference. At the same time, laser light is incident through the opening 32' of the electrode 3' to cause SPR.

Figure 6:
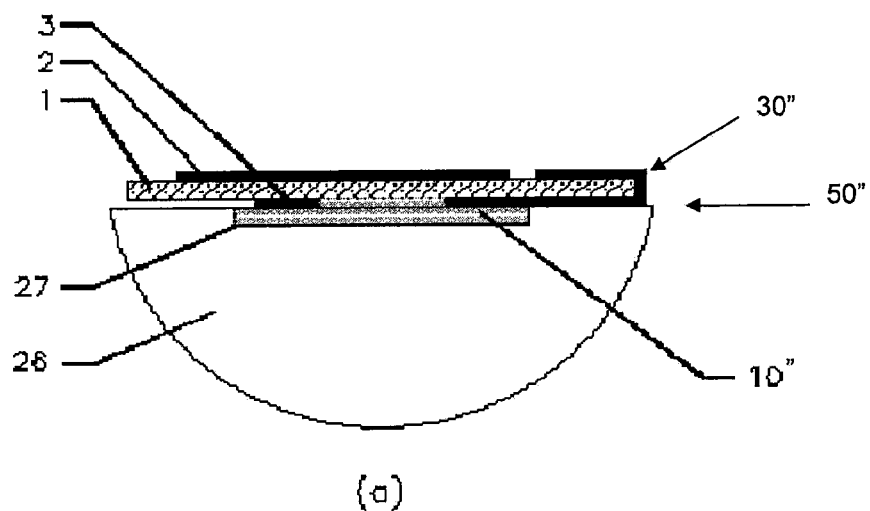
Figure 6:
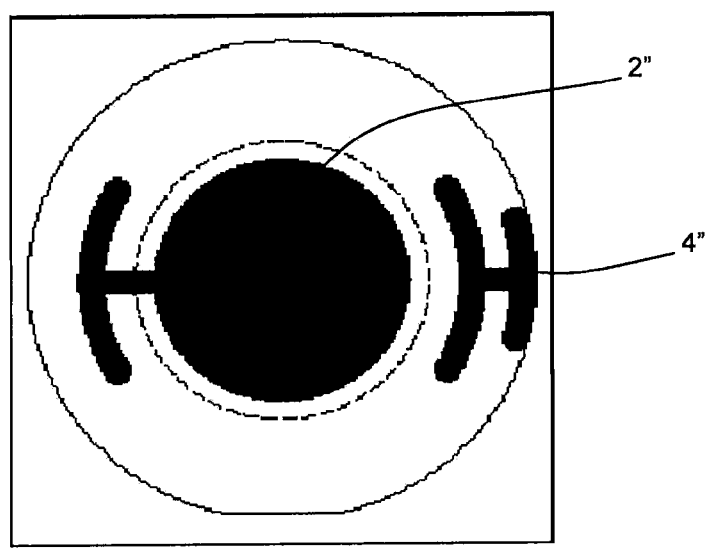

FIG. 6 is a cross-sectional view of a disk arrangement 50" that is compact and which may be disposable. The disk arrangement 50" includes sensor chip 30". In this embodiment, the sensor chip 30" is functionally similar to the sensor chip 30 and thus like elements are labeled with like reference numerals followed by two prime (') symbols. However, it will be recognized that some differences in structure exist between the sensor chip 30 and the sensor chip 30". For example, this embodiment shows a shallow cavity 27" provided in the prism 26".

The prism 26" is a molded plastic prism 26" having a refractive index of about 1.54 so that it is matched to the quartz substrate 1". The shallow cavity 27" is provided at the center part of the base of the hemispherical prism 26". Like the sensor chip 40' described above, the cavity 27" is filled with an index matching liquid 10", which is a low viscosity and low density liquid, and which is covered by the sensor chip 50".

The optical matching liquid 10" is sealed within the cavity 27" by a suitable sealant to prevent it from leaking or evaporating from the cavity.

FIG. 7 depicts another embodiment of an analytical device 60''' that includes a sensor chip 30'''. In this embodiment, the sensor chip 30''' is functionally similar to the sensor chip 30 and thus like elements are labeled with like reference numerals followed by three prime (') symbols. However, this embodiment includes a waveguide 28'''.

The sensor chip 30''' is attached to a prism 11''' on one side and a sample receiving cell in the form of cell 5''', which is filled with an analyte sample 8''' and which operates in the same manner as the system 36 described with reference to FIG. 3 above.

Accordingly, the disk arrangement 30''' is capable of undertaking combined SPR and QCM analytical techniques. As shown in FIG. 7, in this embodiment a suitable waveguide 28 is coated onto the sensing electrode 2'''. The analyte solution 8''' is exposed to the waveguide 26''', leading to an ATR induced waveguide-based SPR analysis. The waveguide is made from multiple layers of rigid solid film. In this embodiment, the total thickness of the waveguide is in the range of from 1 micrometer to 2 micrometers. It has been found from the inventors' experience that for solid film, QCM is able to detect up to 10 micrometers.

FIG. 8 shows a perspective view of a combined SPR and QCM sensor chip 30^. In this embodiment, the sensor chip 30^ is functionally similar to the sensor chip 30 and thus like elements are labeled with like reference numerals followed by the (^) symbol. The sensor chip 30^ is capable of receiving multiple channels of SPR measurement due to the larger sized opening 32^ relative to the opening 32 of the other electrodes (3,3',3'',3'''). The opening 32^ is large enough for multiple light beams to pass through to enable multi-channel SPR measurement to be carried out to gain more information of the interface of the electrode 2^ and quartz crystal substrate 1^.

FIG. 9A is a cross-sectional view of another embodiment of a sensor chip 30^^. In this embodiment, the sensor chip 30^^ is functionally similar to the sensor chip 30 and thus like elements are labeled with like reference numerals followed by two (^^) symbols. The disk arrangement 30^^ includes an array of metal electrodes provided on a quartz substrate 1^^. The quartz substrate 1^^ includes an array of electrodes (2^^, 3^^).

FIG. 9B shows a plan view of the top surface of the quartz substrate 1^^ having a plurality of electrodes 2^^ provided thereon. FIG. 9C shows a plan view of an array of electrodes 3^^ with their openings 32^^ provided therein on a bottom surface of the quartz substrate 1^^.

It will be appreciated that the combined SPR and QCM sensor chips (30,30',30'',30''',30^,30^^) disclosed herein can be ATR coupled to a prism, a focus lens, or waveguide. The sensor chips (30,30',30'',30''',30^,30^^) can be single mode or multi-mode in that they are capable of receiving single or multiple incident light beams.

The sensors used disclosed herein can be used for detection of adsorption from both liquids and gases. It will be appreciated by persons skilled in the art that numerous variations and/or modifications may be made to the invention as described herein without departing from the spirit or scope of the invention. The present embodiments are therefore to be considered in all respects as illustrative and not restrictive.

Fabricating Sensor Chip Assembly

The disclosed sensor chip assemblies may be fabricated as follows.

A quartz crystal substrate can be obtained commercially such as, for example, from Maxtek, Inc. of Santa Fe Springs, United States of America. The quartz crystal substrate is planar and in a disk shape. The quartz crystal substrate can be obtained pre-cut or cut to a required size.

Approximately 50 nm of metal is vapor deposited on a first side of the planar crystal substrate to form the first thin film metal electrode (2,2',2",2'",2^,2^^). A circular patch may be placed on the opposite surface of the electrode before vapor deposition of a further 50 nm on the second opposite face of the substrate to form the second thin film metal electrode (3,3',3",3'",3^,3^^). The patch is then removed to reveal an opening (32,32',32",32'",32^,32^^). A layer of metal (4,4',4", 4'",4^,4^^) is be deposited on a side of the substrate 1 to connect the electrodes (2,2',2",2'",2^,2^^) and (3,3',3",3'",3^, 3^^).

The Kretschmann prism (11,11',11",11'",11^,11^^) is commercially available from Hellma optik Gmbh of Jena Germany. The Kretschmann prism (11,11',11",11'",11^,11^^) is coupled to the electrode (3,3',3",3'",3^,3^^) by a prism holder. The light coupling medium (10,10',10",10'",10^,10^^) is injected between the Kretschmann prism (11,11',11",11'", 11^,11^^) and the electrode (3,3',3",3'",3^,3^^) and is sealed such as by O-rings 7.

Index Matching Fluid

The oscillation quality of QCM signals generated from liquid samples is mainly determined by the viscosity and density of the liquid. In known sensors for QCM adsorption analysis, one face of the substrate is exposed to the sample liquid and the other side of the substrate to air. For most biological adsorption analysis, for example, phosphate buffered saline (PBS) is the frequently used medium, under which the QCM quality factor is about 25000 (ie such as for a 10 MHz QCM from International Crystal Manufacturing Co., Inc. of Oklahoma City, United States of America). This oscillation quality is sufficiently stable and the frequency measurement is precise. For the same 10 MHz QCM, when one face is exposed to PBS and the other side to an index matching oil, the Q drops badly below 500. The 5 times lower Q factor means a 5 times broadening of the frequency spectrum, which makes stable oscillation and precise frequency measurement difficult, if not impossible. Moreover when the QCM is placed on a prism through a highly viscous index matching oil, the drastic damping effect makes the oscillation barely detectable.

In the present embodiments, a low viscose liquid is used as an index matching fluid rather than oil. Table 1 shows the material properties of a few organic solvents that can be used for light coupling in the disclosed embodiment. The measured QCM quality factors (10 MHz ICM QCM) under different exposure condition are also included in Table 1.

TABLE 1

| Exposure Conditions | Liquid density of organic solvent (g/cm$^3$) | Viscosity of organic solvent (cP) | Refractive Index of the organic solvent (@$\lambda$ = 632.8 nm) | Q factor (×1000) |
|---|---|---|---|---|
| PBS/Air | | | | ~2.5 |
| PBS/Styrene | 0.907 | 0.76 | 1.55 | ~1.38 |
| PBS/Toluene | 0.867 | 0.58 | 1.49 | ~1.35 |
| PBS/Benzyl alcohol | 1.540 | 5.0 | 1.54 | ~0.7 |
| PBS/IMO | 0.820 | 100 | 1.51 | ~0.5 |

Where "PBS" is Phosphate-Buffered Saline and "IMO" is Index Matching Oil.

Example 1

In example 1, SPR and QCM measurements were generated using the same sensor system arrangement as described above with reference to FIG. 3. Accordingly, the sensor system arrangement for this example will be described with reference to FIG. 3 using the same reference numerals.

Simultaneous SPR and QCM measurements were obtained using gold-coated quartz disks as the substrate. The ATR SPR was generated from the electrode 2 on the first side of the quartz substrate 1. The QCM oscillation was driven by the application of an AC voltage over the quartz substrate 1 through the electrodes (2,3). For ATR SPR excitation, an index matching liquid in the form of index matching toluene (10) was sealed between O-rings (7). Toluene is an electrically non-conductive and has low viscosity and low density relative to water. The index matching toluene acts as a passive light coupling interface for excitation of surface plasmon resonance.

In this example, the substrate 1 is a 6 MHz AT-cut quartz plate having a thickness of 0.276 mm and a diameter of 25.4 mm. The a layer of 45 nm gold with a 5 nm Cr adhesion layer was deposited on the quartz substrate 1 to form the thin film electrode 2. A gold electrode layer having an opening with an internal diameter of 6.35 mm was deposited on the opposite side of the quartz substrate 1 to form thin film electrode 3.

The prism 11 was made from BK7 glass and was disposed adjacent to the electrode 3 with the index matching toluene (10) sealed by the O-ring 7 therebetween.

As light source in the form of a p-polarized He—Ne laser (14) (632.8 nm) from Melles Griot of Carlsbad, Calif., United States of America was used. The light beam 15 from the laser 14 was mechanically chopped in conjunction with a lock-in amplifier before entry into the prism 11. The intensity of the beam reflected at the interface of the gold electrode 2 and the quartz substrate 1 was detected by a photodiode detector and recorded as a function of the incidence angle for the "angular-scan" measurement.

FIG. 10$a$ shows an angular scan curve obtained using index matching toluene (10). The curve of FIG. 10$a$ shows a deep intensity loss at the SPR angle of 43.5 degree. The smooth reflective intensity changes verses the incidence angle indicates that the sensor system 36 achieves excellent light coupling with the index matching toluene.

Example 2

Figure 5:
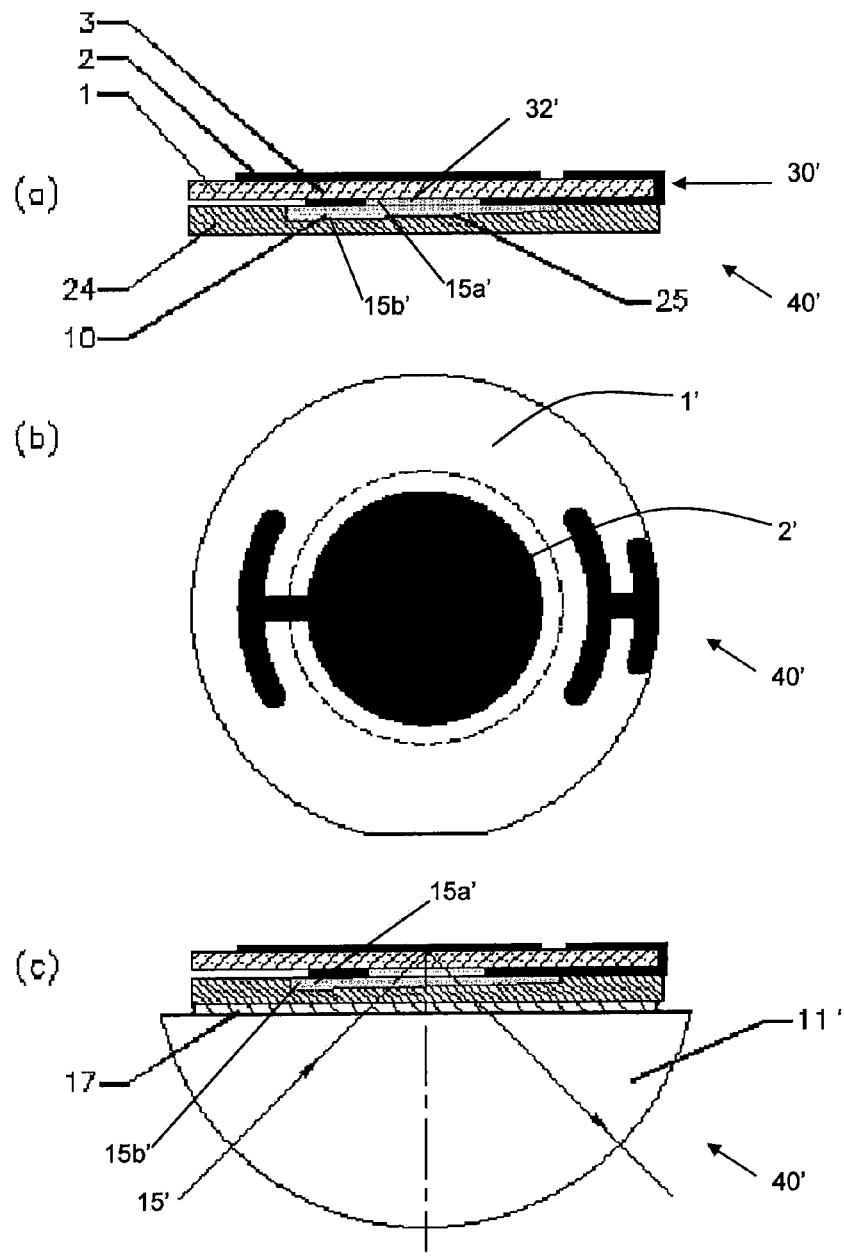

In example 2, the same sensor chip 30' of FIG. 5 was utilised in an AUTOLAB ESPIRIT™ SPR instrument that is commercially available from Eco Chemie B.V. of Utrecht, The Netherlands. Accordingly, the sensor chip 30' for this example will be described with reference to FIG. 5 using the same reference numerals.

In this example, 10 MHz quartz substrate 1' having a thickness of 0.166 mm was placed on the hemispherical prism 11' with a supporting slide 24'. The supporting slide 24' Index matching liquid 10' was injected into the cavity 15$a$'.

FIG. 10$b$ shows the angular scan curves obtained from the sensor chip measured with the Autolab SPR instrument. The Autolab SPR instrument uses a laser diode at a wavelength of 670 nm and a vibrating mirror to modulate the angle of incidence of the p-polarized light beam on the substrate. A full description of the method of generating the SPR is disclosed in Ward et al, Anal. Biochem. 2000, 285, 179, which is incorporated herein for reference.

Three different SPR signals were generated by injecting three different index matching liquids 10' injected into the cavity 15$a$', respectively being toluene, styrene and benzyl alcohol. The SPR spectra for the three index matching fluid can be seen in FIG. 10$b$. Accordingly, the toluene, styrene and benzyl alcohol are shown to be promising solutions as index matching liquids in a sensor chip having a quartz substrate/

BK7 glass prism arrangement. This is because all three liquids show clearly show reflective minima points at their resonant frequencies.

FIG. 10c shows the SPR stability measured from the Autolab SPR. For the standard Autolab system, the baseline SPR angle stability over 30 minutes was about ±0.5 mdegree. When using the sensor chip 30' incorporated with organic solvent for index matching, the baseline stability is about ±2 mdegree, which is favorably acceptable for most of the interface analysis.

Example 3

In this example, QCM oscillation behaviors (oscillation quality and stability) were studied when one face of the quartz substrate was exposed to an aqueous solution and the other face of the quartz substrate the index matching liquid.

Bovine Serum Albumin (BSA) adsorption on QCM was measured using a 10 MHz, AT-cut quartz substrate from International Crystal Manufacturers Inc of Oklahoma City, Okla., United States of America having a thickness of 0.166 mm and a diameter 13.66 mm. Both sides of the quartz were deposited with 100 nm thick gold electrode, the diameter of electrodes were 5 mm and there were no openings on any electrodes.

For in-situ frequency measurement in liquid, the QCM crystals were fixed into two plexiglas blocks with neoprene O-ring seals. The upper face of the quartz formed the base of an open liquid cell and the lower face forms the base of a closed liquid cell. The open cell allowed application liquid up to 1 mL and the closed liquid cell was about 70 µL in volume with an oblique angle. Using this set up, the upper face of the crystal was exposed to PBS buffer solution, while the lower face to air or to non-conductive, low viscosity and density organic solvent. The frequency response was measured with PzTools hardware and software from Universal Sensors, Inc. of Metairie, La., United States of America. Frequency stability was 1 Hz. For impedance analysis, the same setup was connected to an S&A 250B Network Analyzer from Saunders & Associates, Inc of Phoenix, Ariz., United States of America, which recorded the frequency spectrum and impedance parameters, including Q factor. The frequency stability of the Network Analyzer was 4 Hz.

Figure 11:
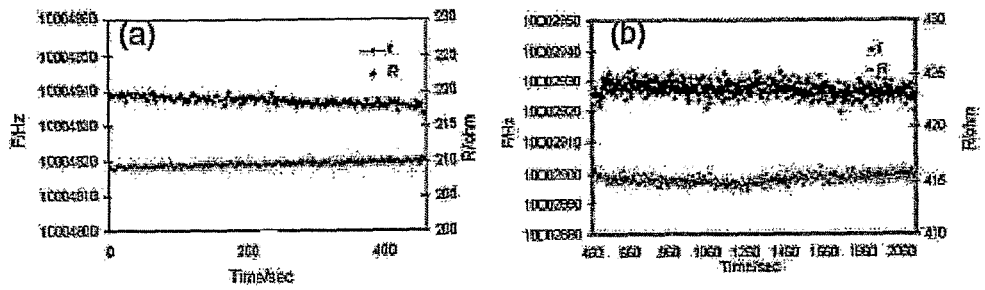

FIG. 11 shows the simultaneous frequency and motional resistance responses of QCMs with the exposures of PBS/air (FIG. 11a) or PBS/toluene (FIG. 11b) measured from the Network Analyzer. The crystal with the lower face exposed to air had a noise level of 4 Hz and a Q factor of 2.5 k (FIG. 11a), and the crystal with the lower face exposed to toluene had a noise level of 10 Hz and a Q factor of 1.35 k (FIG. 11b). When using the PzTools instruments the noise levels were 1 Hz and 3 Hz, respectively.

Example 4

In example 4, SPR measurements were generated using the same sensor system arrangement as described above with reference Example 3.

In example 4, the radial dependent QCM mass sensitivity of the sensor chip 36 was studied for a BSA adsorption reaction. In this example, the BSA adsorption experiment indicated that QCM with this exposure condition was favorably applicable for an actual interfacial analysis. To perform the in-situ protein immobilization, the freshly cleaned QCM crystals were first treated with 10 mM 11-Mercaptoundecanoic acid (MUA) solution for 12-24 hr. After activating the COOH groups on the surface using EDC/NHS chemistry, the sensor was ready for covalent BSA attachment.

A 10 MHz, AT-cut quartz substrate 1 having a thickness of 0.166 mm and a diameter 13.66 mm was used. The 45 nm of gold and 5 nm of Cr were vapor deposited on the substrate to form electrodes (2,3). The electrode 3 included an opening 32 having an internal diameter of 3.5 mm. The 'Dot-ink calibration' method as taught in P. J. Cumpson and M. P. Seah, *Meas. Sci. Technol.* 1990, 1, 544-555, which is incorporated herein in its entirety for reference, was used to study the radial dependent mass sensitivity distribution of the QCMs with the electrode 2 on both sides (P/P electroded QCM) and QCM with electrodes (2,3) (P/R electroded QCM). [NB. P/P stands for plate/plate, where the plate electrode is a solid electrode with no opening. P/R stands for plate/ring, where ring electrode where the ring electrode is an electrode with an opening.] The BSA adsorption reaction was monitored using these QCMs. The experimental setup for BSA adsorption study was the same as described in the Example 3. After pre-treatment of the electrode 2 using MUA, the QCMs are fixed into the Plexiglas block liquid cell and connected to the Network analyzer. The electrode 2 of the QCM was exposed to PBS buffer solution to calibrate the frequency baseline before BSA application.

FIG. 12 shows the frequency response of the activated QCMs to BSA adsorption from the PBS buffer on the upper electrode. In both PBS/air as shown by arrow 70 and PBS/Toluene as shown by arrow 72, the application of BSA solution (5 mg/mL in PBS) results in a steady frequency drop of about 150 Hz at saturation. This indicates an accumulation of the protein molecules on the interface over time. Although the system with the lower face exposed to toluene has higher noise level than the system where the lower face exposed to air, it can be seen from FIG. 12 that sufficient stability and sensitivity in the BSA adsorption measurement is achieved.

It can be concluded that the exposure of the QCM to an appropriate organic solvent will not affect the oscillation quality in interfacial analysis.

FIG. 13 shows the radial dependent mass sensitivity on these QCMs. The bell shaped sensitivity distribution of the P/P electrode QCM reflects the fact that in the shear mode oscillation, more energy is entrapped in the center of the electroded areas. Although the P/R electroded QCM has complicate sensitivity distribution and declined overall mass sensitivity, experiments indicate that these QCMs can still be used to monitor adsorption reactions with a reasonable frequency response.

FIG. 14 shows the frequency response of the P/P as shown by arrow 76 and P/R as shown by arrow 74 electroded QCMs to BSA adsorption reaction. The saturated frequency decreases are 140 Hz/130 Hz (before/after rinsing) and 125 Hz/110 Hz (before/after rinsing) for the P/P and P/R electroded QCM, respectively. Despite the declined signal (about 10%) the frequency response show a similar trend, which is well reflective of the interfacial binding process. B)

Example 5

In example 5, SPR and QCM measurements were generated using the same sensor system arrangement as described above with reference to FIG. 3. Accordingly, the sensor system arrangement for this example will be described with reference to FIG. 3 using the same reference numerals.

Simultaneous SPR and QCM measurements were obtained using gold-coated quartz disks as the substrate. The ATR SPR was generated from the electrode 2 on the first side of the quartz substrate 1. The QCM oscillation was driven by the application of a RQCM instrument obtained from Maxtek Inc of Santa Fe Springs, Calif., United States of America, over the quartz substrate 1 through the electrodes (2,3). The frequency response of the QCM was recorded by the RQCM instrument as well.

For ATR SPR excitation, an index matching liquid in the form of index matching toluene (10) was sealed between O-rings (7). Toluene is an electrically non-conductive and has low viscosity and low density relative to water. The index matching toluene acts as a passive light coupling interface for excitation of surface plasmon resonance.

In this example, the substrate 1 is a 6 MHz AT-cut quartz plate having a thickness of 0.276 mm and a diameter of 25.4 mm. The layer of 45 nm gold with a 5 nm Cr adhesion layer was deposited on the quartz substrate 1 to form the thin film electrode 2. A gold electrode layer having an opening with an internal diameter of 6.35 mm was deposited on the opposite side of the quartz substrate 1 to form thin film electrode 3.

The prism 11 was disposed adjacent to the electrode 3 with the index matching toluene (10) sealed by the O-ring 7 therebetween.

A light source in the form of a p-polarized He—Ne laser (14) (632.8 nm) from Melles Griot of Carlsbad, Calif., United States of America, was used. The light beam 15 from the laser 14 was mechanically chopped in conjunction with a lock-in amplifier before entry into the prism 11. The intensity of the beam reflected at the interface of the gold electrode 2 and the quartz substrate 1 was detected by a photodiode detector, and recorded as a function of the time for the kinetic measurement.

FIG. 15 shows Bovine Serum Albumin (BSA) absorption probed with simultaneously recorded QCM frequency as shown by arrow 78 and SPR reflectivity as shown by arrow 80. The baseline frequency and reflectivity were recorded when the electrode 2 on surface 1 was exposed to Phosphate-buffered saline (PBS) buffer.

After stabilization, BSA (5 mg/mL in PBS) was injected to replace the PBS buffer. At the end of the adsorption, the cell was rinsed with the PBS buffer to remove unstable adsorption.

From FIG. 15 it can be seen that both the frequency and reflectivity indicate the accumulation/desorption of the protein molecules on the gold surface over time.

APPLICATIONS

The disclosed sensor embodiments can be used as biosensors for simultaneous surface plasmon resonance (SPR) and quartz crystal microbalance (QCM) sensing. The sensor embodiments can be for in-situ, label free analysis of binding reactions.

The disclosed sensor embodiments enable the monitoring of interfacial phenomena using two fundamentally different measurement techniques simultaneously. The complementary SPR and QCM signals acquired by the combined device take advantage of the strengths of sensing technique while testing the validity of some assumptions inherent in data analysis.

In the disclosed sensor embodiments, SPR resonation is based on the incidence of laser beams from the back of the sensor chip via the prism, no penetration of light needs to pass into the tested solution and the sensitivity region for the specific substance is restricted to the extension length of an evanescent wave, i.e. the depth of an electromagnetic wave penetrating into the liquid medium from the sensing surface side. Consequently, there will be minimum of influence on the response connected to specifically bound analyte molecules from non-bound sample molecules. More over, as described above, the sensitivity of the SPR devices based on the ATR prism coupler is much higher than the SPR sensors using grating couplers.

It will be appreciated that the disclosed sensor embodiments do not rely on grating structures for coupling to quartz substrates. Accordingly, the SPR measurement of the disclosed embodiments do not rely on the incidence of light beams through the sample solutions. It is not therefore necessary for the sample undergoing analysis in the present disclosed embodiments to be optically transparent.

The disclosed sensor embodiments produce SPR and QCM signals with a lower signal/noise ratio compared to grating couplers.

The disclosed sensor embodiments that utilise the openings on electrodes (3,3',3'',3''',3^,3^^), allow light to pass directly onto the substrate. Accordingly, the disclosed sensor embodiments do not necessarily require the use of transparent indium tin oxide (ITO) electrodes to allow the transmission of laser light therethrough. With ITO films, light at a wavelength of 632.8 nm, the refractive index of Quartz crystal and sputtering deposited ITO thin film is 1.54 and 1.95 respectively. Although the ITO film is very thin (about 100 nm), the refraction caused by unmatched refractive index is significant and results in a low signal/noise ratio.

In one disclosed embodiment, both the quartz substrate is coated with a planar gold electrode on one side and an electrode that includes an opening on the other side. The windowed electrode allows for the laser light to incident through the quartz substrate and to reach the planar gold electrode where the surface plasmon is excited.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A sensor chip assembly for use in a sensor capable of Surface Plasmon Resonance (SPR) and gravimetric sensing of a sample, the assembly comprising:
    a transparent piezoelectric substrate having a first surface and a second surface opposite to the first surface;
    a first thin film metal electrode provided on the first surface of the substrate for contact with said sample and a second thin film metal electrode provided on the second surface of the substrate, said second thin film metal electrode being disposed on said substrate such that a light beam is capable of being transmitted through the second surface of the substrate and reflected from the first thin film metal electrode;
    an attenuated total reflection (ATR) coupler disposed adjacent to the second thin film metal electrode for coupling light to said substrate; and
    a light coupling medium disposed between the ATR coupler and the substrate, said light coupling medium substantially matching the refractive index of the ATR coupler and the substrate and having a low viscosity relative to an index matching oil having a viscosity of 100 cP,
    wherein in use, a gravimetric signal is generated by applying an oscillating electric field to said first and second thin film metal electrodes and an SPR signal is generated by reflecting a light beam from said first thin film metal electrode that has been transmitted through said ATR coupler, said light coupling medium and said substrate.

2. A sensor chip assembly as claimed in claim 1, wherein the second thin film metal electrode includes an opening for allowing a said light beam to pass therethrough.

3. A sensor chip assembly as claimed in claim 1, wherein the second thin film metal opening is large enough to allow multiple light beams to pass therethrough.

4. A sensor chip assembly as claimed in claim 1, wherein a plurality of first or second or both, thin film metal electrodes are disposed on the substrate.

5. A sensor chip assembly as claimed in claim 1, wherein the first and second thin film metal electrodes are electrically coupled to each other.

6. A sensor chip assembly as claimed in claim 1, wherein the light coupling medium has a refractive index in the range selected from the group consisting of: 1.50 to 1.60, 1.51 to 1.59, 1.52 to 1.58, 1.52 to 1.57, 1.52 to 1.56, 1.52 to 1.55, and 1.53 to 1.55.

7. A sensor chip assembly as claimed in claim 1, comprising a transparent block disposed between the ATR coupler and the second thin film metal electrode, the transparent block having a cavity in which the light coupling medium resides.

8. A sensor chip assembly as claimed in claim 1, wherein the ATR coupler is a prism in a Kretchmann configuration.

9. A sensor chip assembly as claimed in claim 1, wherein the prism has a shape selected from the group consisting of: substantially hemispherical, substantially rectangular, substantially square, and substantially cylindrical.

10. A sensor comprising:
a transparent piezoelectric substrate having a first surface and a second surface opposite to the first surface;
a first thin film metal electrode provided on the first surface of the substrate for locating a sample thereon, and a second thin film metal electrode provided on the second surface of the substrate, the first and second thin film metal electrodes capable of being coupled to an oscillator circuit for oscillating an electric field at one or more selected frequencies to thereby cause the substrate to resonate;
an attenuated total reflection (ATR) coupler disposed adjacent to the second thin film metal electrode and capable of optically coupling a light beam, at a plurality of incident angles, from a light beam source to the first thin film metal electrode to generate surface plasmon resonance (SPR) upon excitation; and
a light coupling medium disposed between the ATR coupler and the substrate, said light coupling medium substantially matching the refractive index of the ATR coupler and the substrate and having a low viscosity relative to an index matching oil having a viscosity of 100 cP,
wherein in use, a gravimetric signal is generated by applying an oscillating electric field to said first and second thin film metal electrodes and an SPR signal is generated by reflecting a light beam from said first thin film metal electrode that has been transmitted through said ATR coupler, said light coupling medium and said substrate.

11. A Surface Plasmon Resonance (SPR) and gravimetric analysis sensing method using a sensor comprising a transparent piezoelectric substrate having a first surface and a second surface opposite to the first surface, a first thin film metal electrode provided on the first surface of the substrate, a second thin film metal electrode provided on the second surface of the substrate, an attenuated total reflection (ATR) coupler adjacent to the second thin film metal electrode, and a light coupling medium disposed between the ATR coupler and the substrate, said light coupling medium substantially matching the refractive index of the ATR coupler and the substrate and having a low viscosity relative to an index matching oil having a viscosity of 100 cP, the method comprising:
providing a sample on the first thin film metal electrode;
oscillating an electric field through the first and second thin film metal electrodes at one or more selected frequencies to generate a gravimetric signal;
generating an SPR signal from a light beam reflected from the first thin film metal electrode after being transmitted through said ATR coupler, said light coupling medium and said substrate.

12. A method of fabricating an assembly for use in a sensor capable of Surface Plasmon Resonance (SPR) and gravimetric sensing, the method comprising:
depositing a first thin film metal electrode on a first surfaces of a transparent piezoelectric substrate;
depositing a second thin film metal electrode on a second surfaces, opposite to the first surface, of the substrate such that a light beam is capable of being transmitted through the second surface of the substrate and reflected from the first thin film metal electrode;
attaching an attenuated total reflection (ATR) coupler adjacent to the second thin film metal electrode; and
sealing a light coupling medium disposed between the ATR coupler and the substrate, said light coupling medium substantially matching the refractive index of the ATR coupler and the substrate and having a lower viscosity relative to an index matching oil having a viscosity of 100 cP.

13. A sensor system capable of performing surface plasmon resonance (SPR) and gravimetric sensing on a biological, biochemical or chemical sample, the sensing system comprising:
a housing having a chamber for locating the sample therein;
a transparent piezoelectric substrate having a first surface and a second surface opposite to the first surface;
a first thin film metal electrode provided on the first surface of the quartz substrate and in fluid communication with the chamber;
a second thin film metal electrode provided on the second surface of the quartz substrate;
an oscillator circuit, coupled to the first and second thin film metal electrodes, for oscillating an electric field at one or more selected frequencies to cause the substrate to resonate at a resonate frequency;
a resonate frequency detector for detecting the resonate frequency to enable a gravimetric signal to be detected;
a light beam source for generating a light beam at a plurality of incident angles;
an attenuated total reflection (ATR) coupler disposed adjacent to the second thin film metal electrode for optical coupling to the light beam source such that an internally reflected light beam is reflected from the first thin film metal electrode at an angle of incidence which will cause surface plasmon resonance (SPR) to occur;
a light coupling medium disposed between the ATR coupler and the substrate, said light coupling medium substantially matching the refractive index of the ATR coupler and the substrate and having a low viscosity relative to an index matching oil having a viscosity of 100 cP; and
a detector for receiving the internally reflected light beam and for detecting the characteristics of SPR that are dependent on the reaction between the sample and the first thin film metal electrode.

14. A sensor system as claimed in claim 13, wherein the second thin film metal electrode includes an opening for allowing a light beam to pass therethrough.

15. A sensor system as claimed in claim 13, wherein a plurality of first or second or both, thin film metal electrodes are disposed on the substrate.

16. A method for Surface Plasmon Resonance (SPR) and gravimetric sensing of a sample liquid using a sensor, the sensor comprising: a transparent piezoelectric substrate having a first surface and a second surface opposite to the first surface, a first thin film metal electrode provided on the first surface of the substrate, a second thin film metal electrode provided on the second surface of the substrate, an attenuated total reflection (ATR) coupler disposed adjacent to the second thin film metal electrode and a light coupling medium disposed between the ATR coupler and the substrate, said light coupling medium substantially matching the refractive index of the ATR coupler and the substrate and having a low viscosity relative to an index matching oil having a viscosity of 100 cP, the method comprising the steps of:

(a) providing the sample liquid on the first thin film metal electrode;

(b) transmitting a light beam through the ATR coupler, the light coupling medium and the substrate;

(c) reflecting the transmitted light from the first thin film metal electrode;

(d) detecting the intensity of reflected light to generate an SPR signal;

(e) applying an electric field across the first and second thin film metal electrodes; and (f) measuring the resonant frequency of the electric field to generate a gravimetric signal.

* * * * *